United States Patent
Jones et al.

(10) Patent No.: US 6,932,083 B2
(45) Date of Patent: Aug. 23, 2005

(54) HOUSING FOR AN INHALER

(76) Inventors: Anthony Patrick Jones, GlaxoSmithKline, Five Moore Dr., P.O. Box 13398, Research Triangle Park, NC (US) 27709; Duncan Robertson, GlaxoSmithKline, Five Moore Dr., P.O. Box 13398, Research Triangle Park, NC (US) 27709

( * ) Notice: Subject to any disclaimer, the term of this patent is extended or adjusted under 35 U.S.C. 154(b) by 75 days.

(21) Appl. No.: 10/203,725

(22) PCT Filed: Feb. 14, 2001

(86) PCT No.: PCT/EP01/01594

§ 371 (c)(1),
(2), (4) Date: Aug. 13, 2002

(87) PCT Pub. No.: WO01/60438

PCT Pub. Date: Aug. 23, 2001

(65) Prior Publication Data

US 2003/0075171 A1 Apr. 24, 2003

(30) Foreign Application Priority Data

Feb. 19, 2000 (GB) .............................. 0003839

(51) Int. Cl.[7] ............................................. A61M 11/00
(52) U.S. Cl. ............................ 128/200.23; 128/200.18; 128/200.21; 128/202.22; 128/205.23; 600/538
(58) Field of Search ................................ 600/538, 540; 482/13; 128/200.14, 200.18, 200.21, 200.22, 200.23, 202.22, 204.23, 204.25, 204.26, 203.12, 205.23

(56) References Cited

U.S. PATENT DOCUMENTS

| | | | | |
|---|---|---|---|---|
| 4,984,158 A | * | 1/1991 | Hillsman ................ | 128/200.14 |
| 5,167,506 A | * | 12/1992 | Kilis et al. ................... | 434/262 |
| 5,333,106 A | * | 7/1994 | Lanpher et al. ............. | 600/538 |
| 5,363,842 A | | 11/1994 | Mishelevich et al. | |
| 5,544,647 A | * | 8/1996 | Jewett et al. ........... | 128/200.23 |
| 5,622,162 A | * | 4/1997 | Johansson et al. ..... | 128/200.14 |
| 5,676,129 A | | 10/1997 | Rocci, Jr. et al. | |
| 5,941,240 A | * | 8/1999 | Gonda et al. .......... | 128/200.14 |
| 6,358,058 B1 | * | 3/2002 | Strupat et al. .............. | 434/262 |
| 6,651,651 B1 | * | 11/2003 | Bonney et al. ......... | 128/200.23 |

FOREIGN PATENT DOCUMENTS

| | | |
|---|---|---|
| EP | 0 667 168 A | 8/1995 |
| WO | WO 95 07723 A | 3/1995 |

* cited by examiner

*Primary Examiner*—Henry Bennett
*Assistant Examiner*—Andrea M. Ragonese
(74) *Attorney, Agent, or Firm*—J. Michael Strickland

(57) ABSTRACT

There is provided a housing for a dispenser suitable for dispensing medicament, particularly for use in the treatment of respiratory disorders. The housing comprises a body; said body including a support for receipt of said aerosol container; a first outlet port connectable to a first pressure recorder for recording change of pressure on firing of said aerosol container; and a second outlet port connectable to a second pressure recorder for recording air pressure within the body; wherein said first outlet port and said second outlet port are separate such that the change of pressure on firing and the air pressure within the body are individually recordable.

30 Claims, 3 Drawing Sheets

HOUSING FOR AN INHALER

The following is a US National Phase filing made under 35 USC 371 of PCT International Patent Application PCT/EP01/01594, filed Feb. 14, 2001, claiming priority to GB 0003839.8 filed Feb. 19, 2000.

TECHNICAL FIELD

The present invention relates to metered dose inhalers by means of which medicament contained in an aerosol container may be administered to a patient. In particular, the invention relates to the housing for an aerosol container which can be used in a system to train patients in the operation of a medicament dispenser.

BACKGROUND TO INVENTION

It is well known to treat patients with medicaments contained in an aerosol, for example in bronchodilator therapy, by means of an inhalation device. Such devices typically comprise a tubular housing, in which the aerosol container is located with a support, and an outlet tube generally in the form of a mouthpiece leading from the tubular housing. The aerosol containers used in such inhalation devices are designed to deliver a predetermined dose of medicament upon each actuation. When used for dispensing medicaments, the housing is held by the patient in a more or less upright position and the mouthpiece is placed in the mouth of the patient. The aerosol container is pressed towards the support to dispense a dose of medicament from the container which is then inhaled by the patient.

It may be understood that effective delivery of medicament to the patient using an inhalation device as described above is dependent upon the patient's ability to coordinate the actuation of the device with the taking of a sufficiently strong inward breath. The required co-ordination can present difficulties to many patients, particularly young children and the elderly, with the risk that these patients do not receive the appropriate dose of medicament. It is thus desirable to provide a means for the patient and medical professional to monitor the usage of the inhalation device. Such means might be designed for everyday usage, or for use in a system for training patients in the correct operation of the inhaler.

One approach to developing such a training system would be to provide a means for comparing the patient's ability to operate the inhaler, for example as assessed by pressure release profiles, against standard criteria for a given inhaler and to advise the patient accordingly in the use of the inhaler. Such pressure release profiles would be determined by measuring the duration and intensity of the patient's inhalation pressure within the body of the inhaler, together with that on firing the container. However, a technical problem in adopting this approach is encountered in trying to differentiate between the inhalation and firing pressures which coincide as they differ greatly in intensity, leading to inaccuracies in their measurement.

The Applicants have now found that inhalation and actuation pressures in an inhalation device may be individually measured by use of two pressure recorders or transducers connected to separate outlet ports within the housing of the device. The pressure recorders can be connected to a microprocessor which can record the output from the pressure recorders and compare the patient's pressure release profile with standard profiles for the inhaler. Suitable instructions are then issued to the patient on a visual display unit advising them in the operation of the inhalation device. The housing, as described below, may be used in a system by medical professionals to train patients in the correct usage of an inhalation device.

The advantage of the present invention over existing methods which employ a pressure sensor to measure actuation is that the use of two physically separated outlet ports in the housing body enables direct measurement of the inhalation and firing pressures.

This in turn allows for more accurate and reproducible measurement of both the pressures and the timings involved in determining pressure release profiles as opposed to previous methods which involve indirect determination of such profiles.

The use of pressure recorders to measure actuation of inhalation devices is known in the art. For example, in WO 96/16686 a pressure transducer is employed in an inhalation device to record the number of doses used or remaining within the device.

International Application Number PCT/EP99/06249 discloses an indirect method of determining pressure release profiles on dispensing medicament to an inhaling patient by the use of two pressure transducers.

WO 93/12823 describes an inhalation device which provides feedback on its use to both the patient and to the medical professional. The device may be used to instruct patients in the correct operation of the inhaler and can also be employed to monitor patient usage over a fixed period.

The use of air flow sensors and differential pressure transducers within an inhalation device is also disclosed in U.S. Pat. No. 5,735,263. The sensors are used to determine a patient's inspiratory flow profile which is then compared to a standard profile by microprocessor means to assess the optimum time for drug release.

SUMMARY OF INVENTION

According to one aspect of the present invention there is provided a housing for an aerosol container for the delivery of inhalable medicament comprising a body; the body including a support for receipt of the aerosol container; a first outlet port connectable to a first pressure recorder for recording change of pressure on firing of the aerosol container; and a second outlet port connectable to a second pressure recorder for recording air pressure within the body; wherein the first outlet port and the second outlet port are separate such that the change of pressure on firing and the air pressure within the body are individually recordable.

In one aspect, the support defines the first outlet port and the body defines the second outlet port.

In a second aspect the body defines a socket for receipt of a plug having a first duct for communicating with the first outlet port and a second duct for communicating with the second outlet port.

In a further aspect, the support has a passage for delivery of the inhalable medicament or placebo from the aerosol container and the exit of the passage defines a nozzle.

Suitably, the first outlet port communicates with the passage and the diameter of the first outlet port is narrower than the passage. The diameter of the first outlet port is no greater than 0.5 millimeters, preferably being in the range of 0.3 to 0.5 millimeters.

In another aspect, the second outlet port is adjacent to the support.

In yet another aspect, the first outlet port connects to a first pressure recorder and the second outlet port connects to a second pressure recorder.

According to another aspect of the present invention there is provided an assembly comprising a housing as described above and a plug comprising a first duct in communication with the first outlet port and a second duct in communication with the second outlet port. Preferably the plug is reversibly attachable to the socket by a snap-fit connection.

In one aspect, the assembly additionally comprises a first pressure recorder in communication with the first outlet port through the first duct and a second pressure recorder in communication with the second outlet port through the second duct.

In another aspect, the assembly additionally comprises a first strand of tubing which connects to the first duct and a second strand of tubing which connects to the second duct. Preferably the tubing comprises an inert material such as stainless steel or an organic polymer.

In a further aspect, the assembly additionally comprises a first pressure recorder in communication with the first outlet port via the first duct and the first strand of tubing and a second pressure recorder in communication with the second outlet port via the second duct and the second strand of tubing.

Optionally the pressure recorders comprise pressure transducers.

In another aspect, the assembly additionally comprises an electronic processor capable of storing, manipulating and visually displaying data captured by the pressure recorders as pressure release profiles. Preferably the electronic processor compares the pressure release profiles with standard inhalation and firing profiles. The standard profiles are derived from pressure release profiles for specific models of inhalation device.

According to another aspect of the present invention, there is provided a training device comprising an assembly as described above wherein the electronic processor compares pressure release profiles with standard profiles and displays instructions to coordinate inhalation and firing. Preferably educational or games software display instructions to different patient groups such as adults or children.

In one aspect, the electronic processor comprises a personal computer.

In another aspect, the training device described above additionally comprises an aerosol container; preferably the aerosol container provides measured doses. Optionally the training device is actuable in response to the breath of a user.

Optionally the first outlet port and first pressure recorder of the training device may be replaced by a suitable sensor for detecting firing of the device. Such sensors are capable of directly detecting an emission from the aerosol canister. Suitable sensors include electromagnetic radiation, sound, temperature, oxygen concentration, carbon dioxide concentration and moisture sensors which detect the emission of a placebo (as carrier or propellant) or medicament from the aerosol container.

The training device may be suppliable as a kit of parts. In one embodiment, the kit of parts comprises a housing as described above and a first pressure recorder connecting to a first outlet port and a second pressure recorder connecting to a second outlet port. Preferably the kit of parts additionally comprises an electronic processor capable of recording and comparing pressure release profiles.

In a second embodiment, the training device is suppliable as a kit of parts comprising a housing, as described above, and a plug for attachment to the housing having a first duct connecting to a first outlet port and a second duct connecting to a second outlet port. Preferably the kit of parts additionally comprises two pressure recorders, tubing connectable to the plug and an electronic processor which is capable of recording and comparing pressure release profiles.

According to a further aspect of the present invention there is provided the use of a training device described above for dispensing medicament.

According to yet a further aspect of the present invention there is provided the use of a training device, as described above, to train patients in the operation of a medicament dispenser.

DETAILED DESCRIPTION OF THE DRAWINGS

Figure 1:
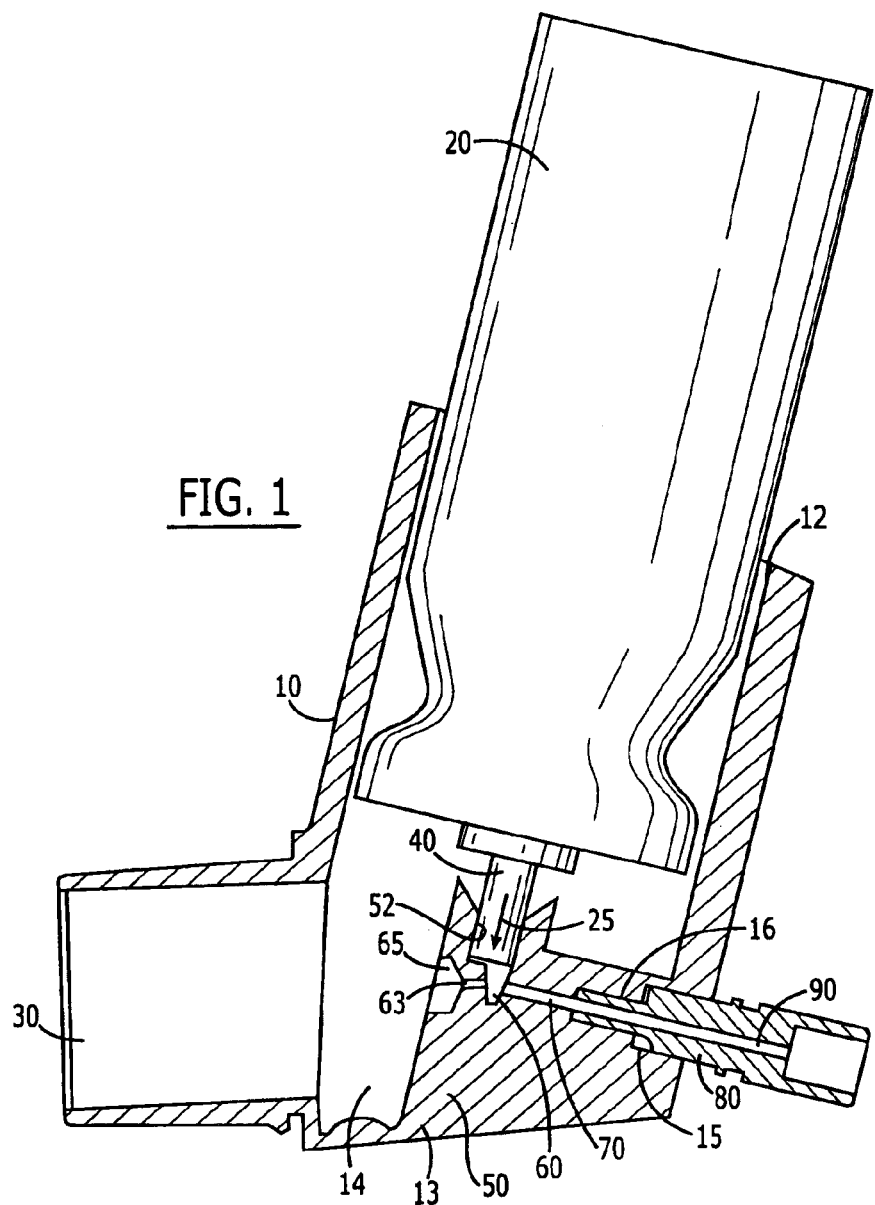
FIG. 1 is a schematic sectional view of the housing, plug and aerosol container according to the invention.

A metered dose inhaler according to the invention is shown in FIG. 1. The inhaler comprises a tubular housing body 10 in which an aerosol container 20 is located. The housing is open at one end 12 (which will hereinafter be considered to be the top of the device for convenience of description) and is closed at the other end 13. An outlet 30 leads laterally from the closed end 13 of the housing 10. In the embodiment illustrated, the outlet 30 is in the form of a mouthpiece intended for insertion into the mouth of the patient but it may, if desired, be designed as a nozzle for insertion into the patient's nostril.

The aerosol container 20 has an outlet valve stem 40 at one end. This valve member can be depressed to release a measured dose from the aerosol container (arrow 25) or, alternatively, the valve stem 40 can be fixed and the main body of the container can be moved relative to the valve member to release the dose.

Figure 2:
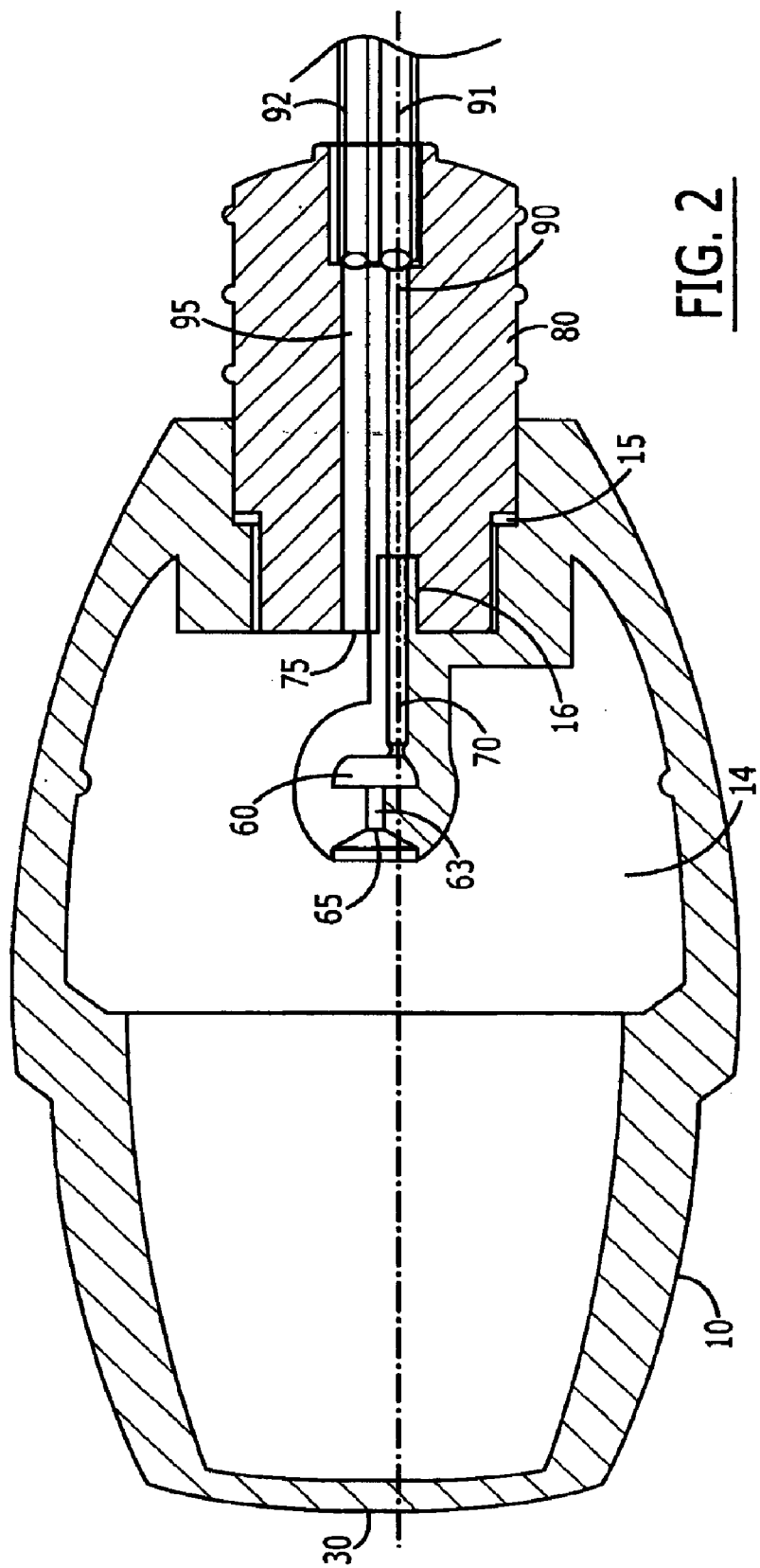
FIG. 2 is a sectional plan view of the housing and plug according to the invention.
Figure 3:
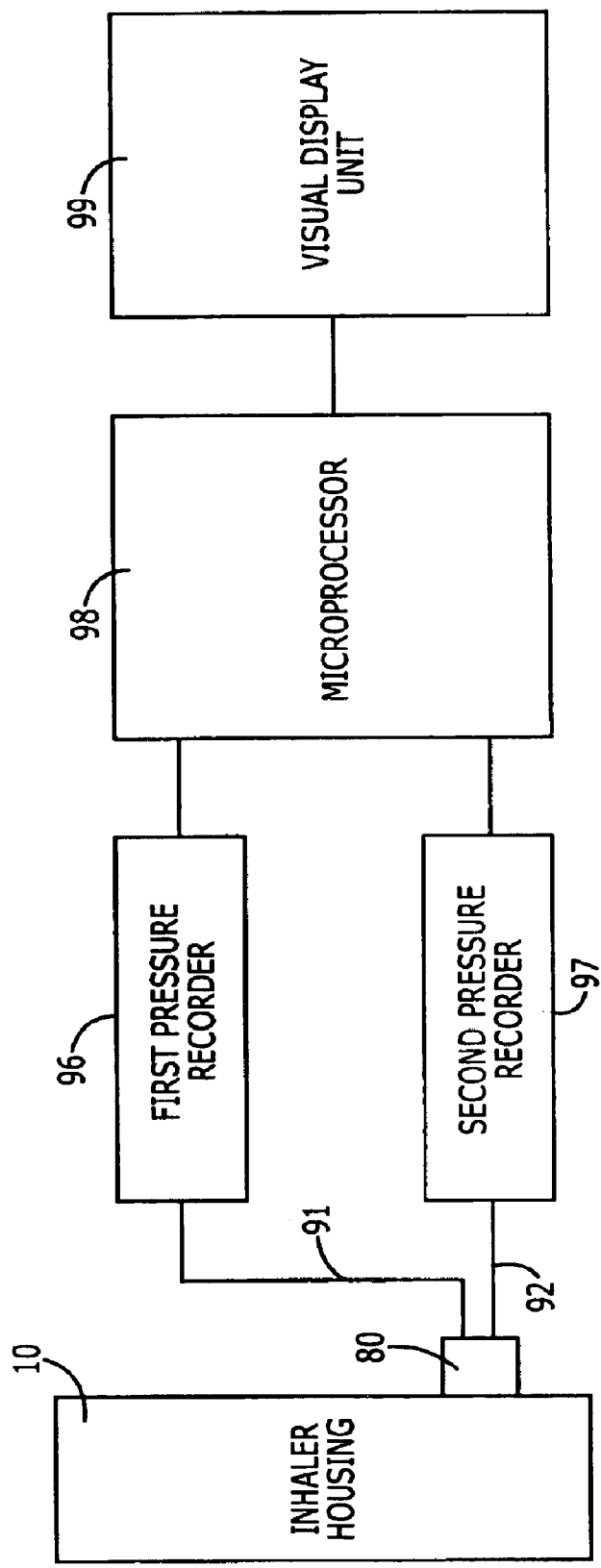
FIG. 3 is a schematic representation of a training device according to the invention.

The invention may be understood by reference to FIGS. 1 through 3. As shown in FIG. 1, the aerosol container 20 is located in the housing body 10 so that one end protrudes from its open top. Spacer ribs (not shown) may be provided inside the housing to hold the external surface of the container 20 spaced from the internal surface of the housing body 10. A support 50 is provided at the lower end of the housing. Support 50 defines a valve stem seat 52, a well 60, a nozzle 65 and a first outlet port 70. Valve stem seat 52 is adapted for receipt and support of valve stem 40 of the aerosol container 20. A well 60 is fluid communication with the valve stem seat 52, and thus the valve stem positioned therein. A passage 63 is provided in the support 50 fluidly connecting nozzle 65 and well 60. The passage 63 being directed towards the interior of outlet 30 through nozzle 65. A first outlet port 70 is in communication with passage 63, via a fluid connection with well 60.

Plug 80, as depicted in FIG. 1, connects to housing body 10 via socket 15. The plug 80 may be reversibly attached to the body 10 by a snap-fit connection 16. Once locked into position, first duct 90 in plug 80 communicates with first outlet port 70.

When the component parts are in the position shown in FIG. 1 the protruding portion of the aerosol container 20 can be depressed, moving the container relative to the valve stem 40 and opening the valve, resulting in the firing of the container and discharge of a measured dose of medicament or placebo 25 (hereinafter referred to as placebo). The placebo dose 25 will be divided into two, the majority of the dose being directed through passage 63 and nozzle 65 into outlet 30 while the remainder is channeled through first outlet port 70 and thence into first duct 90. In this way, the majority of the placebo dose is discharged through nozzle 65 into outlet 30 for inhalation by the patient, while the remaining placebo dose is directed via first outlet port 70 and first duct 90 to the first pressure recorder (not shown). The pressure recorder therefore directly measures the change in pressure on firing of the container.

A sectional plan view of the inhalation device is shown in FIG. 2 comprising a housing body 10 connected to a plug 80 according to the present invention. The plug 80 may be reversibly connected to the housing body 10 through socket 15 by a snap-fit attachment 16. In the position shown, first outlet port 70 communicates with first duct 90 and thence to a first pressure recorder 96 via a tube 91. Furthermore second outlet port 75, which communicates with the interior chamber of inhaler body 10, will now communicate with second duct 95. This duct 95 can in turn be connected to a second pressure recorder 97 for measuring air pressure within the interior chamber 14 of the body of the housing 110.

In operation, the air pressure within interior chamber 14 the body 10 of the inhaler is measured via second outlet port 75 and second duct 95 via tubing 92 by use of the aforementioned second pressure recorder 97. On depression of the aerosol container 20 a measured dose of placebo will be discharged from the container via the valve stem 40 into well 60 where it will then be divided between passage 63 and first outlet port 70. The majority of placebo dose will be channeled through passage 63 and nozzle 65 to outlet 30 for inhalation by the patient. The remaining placebo dose passes through first outlet port 70 and first duct 90 via tubing 91 to first pressure recorder 96 for measurement of the actuation pressure.

It will be understood in another embodiment of the present invention which lacks the plug, which is not illustrated, that the first 70 and second 75 outlet ports may be directly connected to the first and second pressure recorders.

A training device according to the present invention is depicted schematically in FIG. 3. The housing body 10 is connected through plug 80 to a first 96 and a second 97 pressure recorder by tubing 91, 92 which allows direct measurement of the pressures resulting from inhalation by the patient and firing of the aerosol container. The pressure recorders are in turn connected to a microprocessor 98 which is capable of storing and manipulating the pressure data to produce pressure release profiles. These profiles can then be compared with standard inhalation and firing profiles for specific models of inhalers. Standardised profiles can also be generated for patient groups of particular sex, age and body weight for a given inhalation device.

The use of visual display means is of particular utility in the training of patients in the correct operation of the device, since the firing profile, inhalation profile and release profile may all be visually represented on a visual display unit 99. These profiles may be augmented by specific instructions to the patient advising them to synchronize the duration and/or length of inhalation with firing of the aerosol container in order to optimise drug delivery to the lungs. Different software programmes may be used to instruct different patient groups, games software being more appropriate for children while educational software may be more appropriate for adults.

Whilst the present invention has been described in detail in respect of a metered dose inhaler actuable manually by the patient it will be appreciated that other actuation mechanisms can be substituted. In particular, the use of a breath operated inhaler in which the actuation is assisted, and is responsive to, preferably triggered by, the inward breath of the patient, is also envisaged.

It may be appreciated that any of the parts of the metered dose inhaler of the invention which contact the chemical suspension may be coated with materials such as fluoropolymer materials which reduce the tendency of chemical to adhere thereto.

Suitable fluoropolymers include polytetrafluoroethylene (PTFE) and fluoroethylene propylene (FEP). Any movable parts may also have coatings applied thereto which enhance their desired movement characteristics. Frictional coatings may therefore be applied to enhance frictional contact and lubricants used to reduce frictional contact as necessary.

The metered dose inhaler of the invention is in one aspect suitable for dispensing medicament, particularly for the treatment of respiratory disorders such as asthma and chronic obstructive pulmonary disease. Appropriate medicaments may thus be selected from, for example, analgesics, e.g., codeine, dihydromorphine, ergotamine, fentanyl or morphine; anginal preparations. e.g., diltiazem: antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or $6\alpha,9\alpha$-difluoro-11$\beta$-hydroxy-16$\alpha$-methyl-3-oxo-17$\alpha$-propionyloxy-androsta-1,4-diene-17$\beta$-carbothioic acid S-(2-oxo-tetrahydro-furan-3-yl)ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha 4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics and gene therapies. It will be clear to a person skilled in the art that, where appropriate, the medicaments may be used in the form of salts. (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant. Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

1. A housing for an aerosol container for the delivery of inhalable medicament comprising
   a body defining an internal chamber having an open first end and an outlet;
   said body including a support, said support defining
      a valve stem seat for receipt of a valve stem of an aerosol container,
      a nozzle directed toward said outlet, said nozzle in fluid communication with said valve stem seat, and
      a first outlet port in fluid communication with said valve stem seat, said first outlet port being connectable to a first pressure recorder for recording change of pressure on firing of said aerosol container; and
   a second outlet port in fluid communication with the interior chamber of said body and connectable to a second pressure recorder for recording air pressure within the body;
   wherein said first outlet port and said second outlet port are separate such that the change of pressure on firing and the air pressure within the body are individually recordable.

2. A housing according to claim 1 wherein the support defines a well and the first outlet port extends from said well and the body defines the second outlet port extending from said internal chamber.

3. A housing according to claim 1 wherein the body defines a socket for receipt of a plug having a first duct for communicating with the first outlet port and a second duct for communicating with the second outlet port.

4. A housing according to claim 1 wherein said support has a passage for delivery of said inhalable medicament from said aerosol container.

5. A housing according to claim 4 wherein the exit of said passage defines a nozzle.

6. A housing according to claim 5 wherein the first outlet port communicates with the passage.

7. A housing according to claim 4 wherein the diameter of the first outlet port is narrower than the passage.

8. A housing according to claim 1 wherein the second outlet port is adjacent to the support.

9. A housing according to claim 1 wherein the first outlet port connects to a first pressure recorder and the second outlet port connects to a second pressure recorder.

10. An assembly comprising a housing according to claim 1 and a plug comprising a first duct in communication with the first outlet port and a second duct in communication with the second outlet port.

11. An assembly according to claim 10 wherein said plug is reversibly attachable to said socket by a snap-fit connection.

12. An assembly according to claim 10 additionally comprising a first pressure recorder in communication with the first outlet port through said first duct and a second pressure recorder in communication with the second outlet port through said second duct.

13. An assembly according to claim 10 additionally comprising a first strand of tubing which connects to the first duct and a second strand of tubing which connects to the second duct.

14. An assembly according to claim 13 wherein said tubing comprises an inert material such as stainless steel or an organic polymer.

15. An assembly according to claim 13 additionally comprising a first pressure recorder in communication with the first outlet port via the first duct and the first strand of tubing and a second pressure recorder in communication with the second outlet port via the second duct and the second strand of tubing.

16. An assembly according to claim 9 wherein said pressure recorders comprise pressure transducers.

17. An assembly according to claim 9 additionally comprising an electronic processor capable of storing, manipulating and visually displaying data captured by the pressure recorders as pressure release profiles.

18. An assembly according to claim 17 wherein said electronic processor compares said pressure release profiles with standard inhalation and firing profiles.

19. A training device comprising an assembly according to claim 18 wherein the electronic processor compares pressure release profiles with standard profiles and displays instructions to coordinate inhalation and firing.

20. A training device comprising an assembly according to claim 17 wherein educational or games software display said instructions to different patient groups such as adults or children.

21. A training device comprising an assembly according to claim 17 wherein the electronic processor comprises a personal computer.

22. A training device comprising an assembly according to claim 1 additionally comprising an aerosol container.

23. A training device according to claim 22 wherein said aerosol container provides measured doses.

24. A training device according to claim 22 actuable in response to the breath of a user.

25. A kit of parts comprising a housing according to claim 1 and a first pressure recorder connectable to the first outlet port and a second pressure recorder connectable to the second outlet port.

26. A kit of parts according to claim 25 additionally comprising an electronic processor capable of recording and comparing pressure release profiles.

27. A kit of parts comprising a housing according to claim 1 and a plug for attachment to said housing having a first duct connectable to the first outlet port and a second duct connectable to the second outlet port.

28. A kit of parts according to claim 27 additionally comprising two pressure recorders, tubing connectable to said plug and an electronic processor which is capable of recording and comparing pressure release profiles.

29. Use of a training device according to claim 22 for dispensing medicament.

30. Use of a training device according to claim 22 to train patients in the operation of a medicament dispenser.

* * * * *